United States Patent [19]

Paul et al.

[11] Patent Number: 5,633,137
[45] Date of Patent: May 27, 1997

[54] METHOD FOR MEASURING SPECIFIC GENE EXPRESSION: TRANSCRIPTIONAL ACTIVITY PER GENE DOSE

[75] Inventors: John H. Paul; Scott L. Pichard, both of St. Pete, Fla.

[73] Assignee: The University of South Florida, Tampa, Fla.

[21] Appl. No.: 375,259

[22] Filed: Jan. 19, 1995

Related U.S. Application Data

[63] Continuation of Ser. No. 156,868, Nov. 19, 1993, abandoned, which is a continuation of Ser. No. 984,094, Dec. 1, 1992, abandoned.

[51] Int. Cl.⁶ ..................................... C12Q 1/68
[52] U.S. Cl. ............................... 435/6; 935/78
[58] Field of Search ............... 435/6, 91.2; 436/501; 935/77, 78

[56] References Cited

U.S. PATENT DOCUMENTS 5,021,335 6/1991 Tecott et al. .

OTHER PUBLICATIONS

Pardridge et al., J. Biol. Chem 265:18035–18040 (1990) "Brain–Type Glucose–Transporter . . . ".
Goodman et al., Mol Endocrinol 4:1661–1670 (1990) "Transcriptional analysis of the Mouse . . . ".
Grimes et al. Analy. Bio Chem. 172:436–444 (1988) "A total Extract Dot Blot Hybridization . . . ".
Pichard, S.L. and Paul, J.H., Detection of Gene Expression in Genetically Engineered Microorganisms and Natural Phytoplankton Populations in the Marine Environment by Messenger RNA Analysis. Appl. Environ. Microbiol. 57:1721–1727 (1991).

(List continued on next page.)

*Primary Examiner*—George C. Elliott
*Attorney, Agent, or Firm*—Kohn & Associates

[57] ABSTRACT

A method of detecting the level of transcriptionally-related gene expression from a population of cells includes the steps of isolating mRNA and DNA from a population of cells, quantifying the amount of a specific subpopulation of target mRNA transcribed from the target DNA and normalizing the amount of quantified target mRNA to target DNA for measuring transcriptional activity of the target DNA; a measure of gene expression per gene dosage.

8 Claims, 7 Drawing Sheets

OTHER PUBLICATIONS

Chomczynski, P. and Sacchi, N., Single–step Method of RNA Isolation by Acid Guanidium Isothiocyanate–phenol–chloroform Extraction Anal. Biochem. 163:156–159 (1987).

Rymaszewski, Z., Abplanalp, W.A., Cohen, R.M. and Chomczynski, P., Estimation of Cellular DNA Content in Cell Lysates Suitable For RNA Isolation. Anal. Biochem. 188:91–96 (1990).

Raha, S., Merante, F., Proteau, G. and Reed, J.K., Simultaneous Isolation of Total Cellular RNA and DNA From Tissue Culture Cells Using Phenol and Lithium Chloride. GATA 7(7):173–177 (1990).

Karlinsey, J., Stamotoyannopoulos, G. and Enver, T., Simultaneous Purification of DNA and RNA From Small Numbers of Eukaryotic Cells. Anal. Biochem. 180:303–306 (1989).

Zarlenga, D.S. and Gamble, H.R., Simultaneous Isolation of Preparative Amounts of RNA and DNA From *Trichinella Spiralis* by Cesium Trifluoroacetate Isopycnic Centrifugation. Helminthic Diseases Lab., Animal Parasitology Inst., Agriculture Res. Serv., U.S. Dept. of Agr. (1986).

Atlas, R.M. and Sayler, G.S., Tracking Microorganisms and Genes in the Environment. Dept. of Biol., Univ. of Louisville, Louisville, KY; Grad. Ecol. Prog., Univ. of Tennessee, Knoxville, TN.

Fleming, J.T. and Sayler, G.S., Isolation and Characterization of mRNAs Transcribed by Catabolic Genes From Soil Sediment Microorganisms Abstr., Ctr. for Environ. Biotech., The Univ. of Tenn., Knoxville, TN (1990).

Tsai, Y.L., Park, M.J. and Olson, B.H., Rapid Method For Direct Extraction of mRNA From Seeded Soils. Appl. and Environ. Microbiol., pp. 765–768, Mar. 1991.

Tsai, Y.L. and Olson, B.H., Effects of $Hg^{2+}$, $CH_3\_HG^+$, and Temperature on the Expression of Mercury Resistance Genes in Environmental Bacteria. Appl. and Environ. Microbiol. pp. 3266–3272, Nov. 1990.

Oelmüller, U., Krüger, N., Steinbüchel, A. and Friedrich, C.G., Isolation of Prokaryotic RNA and Detection of Specific mRNA With Biotinylated Probes. Journal of Microbiol. Methods 11 (1990) 73–84.

Pichard et al., Applied Environmental Microbiology, vol. 57, pp. 1721–1727; 1991.

METHOD FOR MEASURING SPECIFIC GENE EXPRESSION: TRANSCRIPTIONAL ACTIVITY PER GENE DOSE

This is a continuation of applications Ser. No. 08/156,868 filed on Nov. 19, 1993, now abandoned which is continued of Ser. No. 984,094 filed on Dec. 1, 1992, now abandoned.

TECHNICAL FIELD

The present invention relates to methods of detecting gene expression of functioning organisms in their respective environments. More specifically, the present invention provides a means of detecting the level of gene expression of a specific population of cells in response to environmental stimuli.

BACKGROUND OF THE INVENTION

The detection of gene expression is paramount for the detection of the functioning of organisms in their respective environments. There is a great commercial interest in being able to detect the effects of certain environmental stimuli, such as environmental contaminations, on populations of cells in the environment (both aquatic and terrestrial environments). For example, there is great commercial interest in quantifying the effect of various types of commercial dumping in bodies of water, such as gulfs and oceans, on these ecosystems.

Specific applications of the measurement of gene expression include 1) the functioning of bacteria in fermentors for the production of biotechnological products; 2) the detection and measurement of microorganism activity in the environment, either for bioremediation, activity of genetically engineered organisms for agricultural, or pesticide activity; and 3) the measurement of activity of natural microbial components of ecosystems, including nitrogen fixing organisms, carbon dioxide fixing organisms (to assess the impact of greenhouse gases and their bioremediation), sulphate-reducing organisms, nitrate-reducers, nitrifiers etc.

An integral part of all gene expression methodologies is the isolation of mRNA. When a gene is active, the first process following gene activation is the synthesis of mRNA on a DNA template. This process is termed "transcription". If the mRNA is isolated and probed with a probe which is homologous to the mRNA, the total amount of mRNA can be quantified and the extent of expression of the target gene determined. Unlike the detection of activity for a particular enzyme, where there are different reagents, detection systems etc. which are needed, only one basic technology is needed to detect expression at the mRNA level of any gene in all organisms.

Currently, technology exists for the rapid isolation of mRNA from eucaryotic cells. This process involves guanidinium-isothiocyanate extraction followed by chromatography on polydT cellulose or some other support that takes advantage of the fact that all eucaryotic mRNA's have polyA tails.

No simple technology exists for the isolation of procaryotic (bacterial) mRNA because procaryotic mRNA lack polyA tails. Additionally, bacterial cell walls are more refractile than eucaryotic cells and require some degree of mechanical disruption. Thus, the present invention combines guanidinium-isothiocyanate extraction with mechanical disruption for RNA isolation from procaryotic cells.

Target gene mRNA isolation, detection, and quantification is not enough to determine the level of gene expression by specific microorganisms. For example, a high concentration of mRNA of a target gene may be only the result of a large concentration of cells. Prior art methods can only determine total mRNA content but cannot determine whether a single cell is producing a tremendous amount of mRNA or a whole population of cells is producing a very small amount mRNA. It is conceivable that a sample from an environment may yield a high target mRNA level because it has a very large quantity of cells with a low level of gene expression. Thus, it is essential to normalize the amount of mRNA present to the number of target cells. Typically, this has been done by normalizing mRNA to 23S rRNA content on gels. Although this may be an accurate method for pure cultures, this method will not function to provide useful data in mixed cultures or in the environment where a large amount of nontarget 23S rRNA will be present.

Various prior art methods have been used for the isolation of mRNA. For example, Pichard and Paul (1) disclosed the extraction of mRNA from procaryotic organisms using a modification of method of Chomczynski and Sacchi (2) combined with radio-labeled sense and antisense RNA probes to detect expression of specific genes in isolated indigenous populations of microorganisms. The reference does not disclose any further steps for combining the extraction of DNA from an additional aliquot of the same sample with sense or antisense RNA probe to quantitate expression of specific DNA sequences, target genes, and from this, information determining the amount of specific RNA expressed per target gene DNA in a mixed cell population.

Rymaszewski et al. (3) discloses a method of measurement of DNA content in cell lysates prepared for subsequent isolation of mRNA from the same sample of eucaryotic cell lines or cell cultures. The total DNA content is determined in the quantitation of cellular mRNA in relation to total cellular DNA content is made. The reference does not mention the determination of the level of the specific mRNA in relation to its specific DNA sequence (gene dose).

Raha et al. (4) discloses a method for the simultaneous extraction of total cellular RNA and DNA from the same sample as do the Karlinsey et al. reference (5) and the Zarkenga and Gamble reference (6). The isolated RNA and DNA is suitable for dot blot analysis. Neither reference shows or suggests the determination of the level of specific mRNA expression in relation to its specific DNA sequence by the use of radio-labeled sense or antisense RNA probes.

Atlas and Sayler (7) disclosed the direct extraction of DNA from environmental samples (i.e. mixed cell population) coupled with dot blot hybridization of radio-labeled DNA probe as a method for monitoring the presence of a specific DNA sequence, target gene, in the environment. The reference does not suggest or show monitoring of radio-labeled sense or antisense RNA probes to determine the level of mRNA expression of a specific DNA sequence.

The following references provide technical background for the present invention but are no more pertinent with regard to the patentability of the present invention than those references discussed above: Fleming, J.T. et al. (8); Tsai, Y-L et al. (9); Tsai, Y-L et al. (10); Oelmuller, U. et al. (11); and U.S. Pat. No. 5,021,335 to Tecott et al.

No prior art reference solves the problem of detecting gene expression in mixed cultures or in the environment which is adequate for the commercial applications discussed above. The present invention provides a novel solution to the problem by determining the target, or gene specific mRNA per target DNA or gene expression per gene dosage of sample. This is the most accurate measure of transcriptional activity in the gene expression providing significantly more useful information than the prior art methods set forth above.

SUMMARY OF THE INVENTION

In accordance with the present invention, there is provided a method of detecting the level of gene expression, the method including the steps of isolating mRNA and DNA from a population of cells, quantifying the amount of mRNA and DNA of a specific subpopulation of target mRNA transcribed from the target DNA and normalizing the amount of quantified target mRNA to DNA for measuring transcriptional activity of the target DNA as a specific measure of gene expression.

FIGURES IN THE DRAWINGS

Other advantages of the present invention will be readily appreciated as the same becomes better understood by reference to the following detailed description when considered in connection with the accompanying drawings wherein:

FIG. 2 shows organization of the RuBPCase (carbon fixation) gene operon in phytoplankton. Both the RuBPCase large subunit (rbcL) and the small subunit (rbcS) are cotranscribed, producing a 2.2 Kb transcript and smaller processed transcripts (1.3 kb and 0.9 Kb for the large and small subunits respectively), in the cyanobacterium Synechococcus sp PCC6301. In chlorophytes (green algae) these genes are segregated with rbcL being chloroplast encoded and rbcS nuclear encoded. Despite this difference in structure, sequence analysis has shown that rbcL gene is conserved from cyanobacteria through chlorophytes to higher plants. However, rbcL is divergent with respect to diatoms, rhodophytes and perhaps dinoflagellates forming a separate lineage. We have subcloned the Synechococcus sp. PCC 6301 rbcL gene to form a construct as in FIG. 1A enabling the synthesis of AS and S rbcL gene probes for analyzing natural phytoplankton population gene expression;

DETAILED DESCRIPTION OF THE INVENTION

Generally, the present invention provides a method of detecting the level of gene expression, particularly in response to an environmental stimuli in order to detect functioning organisms in their respective environments. By level of "gene expression", it is meant the quantity or amount of specific mRNA transcribed from a specific gene. That is, the isolation of the mRNA transcribed from a specific gene is used as a marker for the expression of that target genes expression when isolated from a known number of cells from a purified cell population. The amount of specific mRNA can be quantified and the level of expression per unit DNA of the target gene can be determined.

The general steps of the present invention are 1) the isolation of mRNA and DNA from a population of cells; 2) the quantification of the amount of a specific subpopulation of target mRNA transcribed from the target DNA; and 3) the normalization of the amount of quantified target mRNA and DNA which is a measurement of transcriptional activity of the target DNA and a specific measure of gene expression.

The preferred method of isolation of mRNA is a modification of the method of Chomczynski and Sacchi (2). More specifically, the following is a rapid method for direct extraction of RNA from planktonic microbial populations.

Protocol:[1]

[1] All solutions are made with 0.1% Diethyl pyrocarbonate (DEPC) treated water.

1. To sterile 2.2 ml bead beat tubes add 8 scoops glass beads[2] (approximately 0.5 g) and 0.5 ml GIPS[3].

[2] Glass beads (0.1 mm bead dia.) are baked for four hours at 450° C.
[3] The extraction reagent (GIPS) is 4M Guanidinium thiocyanate, 25 mM sodium citrate pH 7, 0.5% sarcosyl, and 0.1M mercaptoethanol.

2. DEPC is added to 0.1% to the water sample and the sample is then filtered through a 25 mm Durapore filter[4].

[4] Millipore 0.45 or 0.22 μm Durapore filters are autoclaved.

3. The filter is rolled and placed in the bead beat tube and 0.05 ml sodium acetate pH 4, 0.5 ml Phenol (water sat.), and 0.1 ml chloroform:isoamyl alcohol (49:1) is added.
4. Bead beat the sample for two minutes and place on ice for fifteen minutes.
5. Microfuge the sample for five minutes and recover the aqueous supernatant (0.5 ml). The sample is reextracted two more times with the guanidinium reagent and the supernatants are combined and precipitated with one volume of isopropanol for a minimum of two hours at −20° C.
6. Microfuge the sample for ten minutes and resuspend the RNA pellet in 0.1% DEPC treated 1 mM ethylene diamine tetraacetic acid (EDTA) pH 7.
7. The sample is reprecipitated with 0.1 volume 2M NaCl, two volumes Ethanol, and glycogen carrier overnight at −40° C.
8. Microfuge the sample to pellet the RNA and wash pellet with one volume 70% ice cold Ethanol.
9. Samples are ready for enzyme digestion, dot/slot blot or northern analysis, S1 nuclease mapping, etc.

The stated protocol uses a type of filter that yields very high recovery of mRNA. A research modification is the sequential addition of reagents for the extraction of mRNA. Simultaneous addition of reagents results in very little recovery of mRNA.

Of course, other methods of RNA isolation can be utilized for various other cell populations, these methods being well known in the art. For example, the Pichard and Paul reference (1) discloses a method of extracting mRNA from procaryotic organisms utilizing a method similar to the one disclosed herein. The other references cited herein also provide other methods of mRNA isolation from various cell populations.

The following is a preferred method for DNA extraction from planktonic microorganisms utilizing a boiling SDS extraction procedure.

DNA Extraction Methodology for Planktonic Microorganisms

1. Filter sample onto Millipore 0.22 or 0.45 μm Durapore filter.
2. Place filter in a sterile bead beat tube and add 1.0 ml sterile STE buffer pH 8.0.
3. Add 10% SDS to a concentration of 1%.
4. Place in boiling water for 2.0 minutes.
5. Microfuge for ten minutes to remove cellular debris.
6. Remove supernatant and repeat the extraction a second time. Precipitate the supernatants with 1/10 volume 3M NaOAc pH 5.0 and two volume ethanol O/N at −20° C.
7. Microfuge sample for ten minutes and wash with one volume of 70% ethanol.
8. Resuspend pellet in sterile deionized water.
9. Sample can then be digested with DNase or RNase, dot blotted and probed. Note: sample is probably not purified enough for restriction analysis.

Quantification of the mRNA and DNA is determined by probing techniques. The mRNA dot blot is probed with a radio-labeled antisense RNA probe with a radio-labeled sense probe as control for DNA contamination, similar to the methods of Frischer et al. (12). Both probes must be of the same total radioactivity. This is essential to quantitate any nonspecific hybridization detected by the sense probe so it can be subtracted from the RNA signal. The DNA dot blots are also probed with either the antisense or sense RNA probes, not being necessary to do both. This is because either sense or antisense probe will bind to DNA. The dot blots are then counted, radioactivity quantitated and compared to standard curves of the specific mRNA and DNA sequence to determine the quantity, generally in the nanogram or picogram range of RNA or DNA per dot blot. This amount is converted to the amount per milliliter of sample. From this information, the amount of specific mRNA per target gene DNA is calculated.

The following is a specific preferred protocol for the quantification of gene expression by normalization of the amount of target mRNA and DNA.

Gene Expression per Gene Dosage in Aquatic Microorganisms

1. RNA sample is taken up in a small volume of DEPC-treated 1 mM EDTA, pH 7.0. (usually 60 μl)
2. The sample is split into three equal aliquots. One aliquot is RNase digested using RNase A. Two μl of 2M MgSO$_4$ and 4 μl of RNase is added to the aliquot and digested for sixty minutes at −37° C.
3. A second aliquot is digested with RNase-free DNase. We recommend RQ1 DNase from Promega. Add 2 μl RNasin Ribonuclease Inhibitor (Promega). Add 2 μl 2M MgSO$_4$. Add 4 μl RQ1 DNase. Incubate sixty minutes at 37° C.
4. The third aliquot is untreated.
5. It is helpful to split all three aliquots in half, to use one half for probing with a sense gene probe, and one half for probing with antisense gene probe.
6. Using a 0.1% DEPC-treated dot blotting apparatus, dot the untreated and the DNase-treated samples. Do this for both halves of the extracts, on separate pieces of charged nylon or on separate areas of the same piece of charged nylon.
7. Remove the charged nylon from the dot-blotter and blot the RNase-treated samples manually. This prevents contamination of the dot-blotter with RNase.
8. Note: it is also convenient to dot a standard curve of pure mRNA of the target gene at this time. Such mRNA can be synthesized in vitro using the Promega pGEM systems.
9. Probe the one half of the extracts with the antisense single strand probe using any probe labelling of choice (eg. $^{35}$S UTP and Promega kit) and the other half of the dotted extracts with the sense probe. The antisense probe will bind with DNA and mRNA. The sense probe will bind with DNA only, and is a control for contamination of the sample with DNA and also nonspecific hybridization. It is essential that the probes be of the same total radioactivity (for reasons set forth previously regarding other probing techniques). Samples are probed at 55° C. in 50% formamide. Washing is one five minute wash in 2X SSC 1 mM dithiothreitol at room temperature, followed by three washes in PSE at 65° C. for one hour each, followed by three washes in PSE at 65° C. for thirty minutes each.
10. Dry dot blots, expose to X-ray film, or use beta scanner to quantitate radioactivity. If very low signals are anticipated, an autoradiographic enhancer should be sprayed over the samples and the samples exposed for up to two weeks. Compare unknowns to standard curve and calculate mRNA signal in ng or pg RNA/dot. Convert to ng or pg RNA/ml sample.

11. Take DNA extracts, split in two equal aliquots. Digest one with RNase-free DNase as described above, and leave the other untreated. Using the dot-blot apparatus, dot the untreated and DNase-digested extracts onto charged nylon. (Note: one can further split the sample and probe with sense and antisense probes, but this is unnecessary). It is convenient to prepare a standard curve at the same time to be probed at the same time. Use purified target gene fragment or else gene in vector, but correct for weight of vector in the latter.

12. Probe with either sense or antisense probe at 42° C. in 50% formamide. Wash using same protocols/conditions/temperature as RNA.

13. Dry filter and either expose to x-ray film or use beta scanner to quantitate radioactivity. Compare unknowns to standard curve and express as ng DNA/dot. Convert to ng or pg DNA/ml sample.

14. To determine gene expression per gene dosage, just divide the quantity of target gene RNA by quantity of target gene DNA. Other RNA extraction protocols may be employed including 8M guanidinium hydrochloride with cesium chloride centrifugation. The DNA may be extracted by a number of ways, including alkaline lysis "miniprep" procedure. The protocols outlined here have been designed for simplicity and to minimize sample loss.

The following experiments demonstrate the utility of the present invention to check levels of gene expression.

Below is a description of how the system efficiently determines levels of specific gene expression (i.e. gene expression per gene dose). The examples given are for two arbitrarily selected genes, but these protocols will work for any target gene which has been identified and has been or can be directionally cloned into vectors containing Sp6 and T7 RNA polymerase promoters.

Figure 1A:
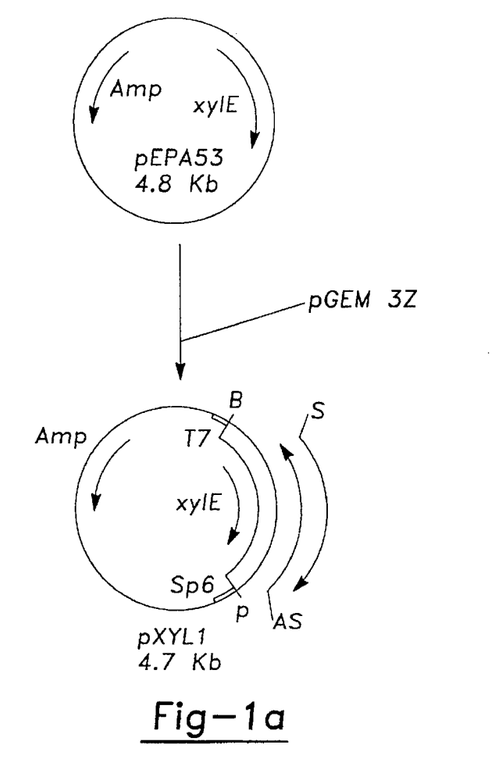
FIG. 1A shows single-stranded RNA probe synthesis. Antisense (AS) probes, complimentary to xylE mRNA, are produced by in-vitro transcription from the Sp6 promoter using the Sp6 RNA polymerase. Likewise, a Sense (S) probe is also constructed using the T7 promoter and T7 RNA polymerase.
Figure 1B:
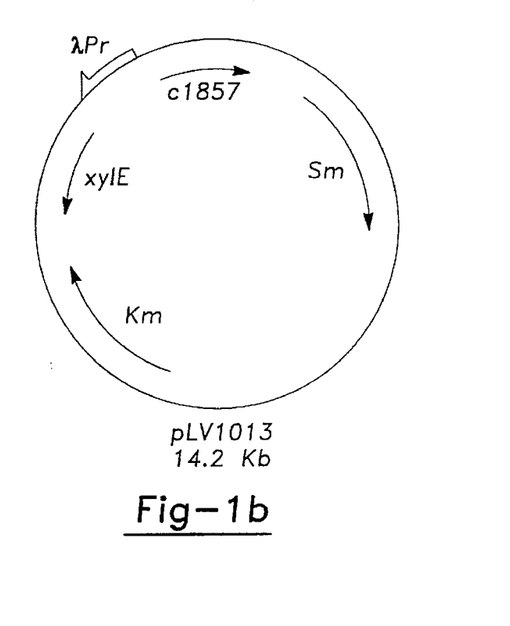
FIG. 1B shows temperature regulated xylE expression construct. In this plasmid (pLV1013) the xylE gene is controlled by the Lambda promoter $P_R$ and its repressor c1857. At 27° C. xylE is not expressed due to proper function of c1857. At elevated temperatures (40° C.) c1857 losses affinity for the Lambda promoter allowing xylE transcription to occur.

FIG. 1 shows plasmids that contain the catechol dioxygenase gene, xylE. The xylE gene was subcloned from the plasmid pEPA53 into pGEM3Z (Promega, Inc.) to form pXYZ1. In the examples given below, a marine Vibrio species has been transformed with the plasmid pLV1013 which contains a temperature sensitive promoter system. This marine Vibrio is used in the ensuing studies.

Figure 4:
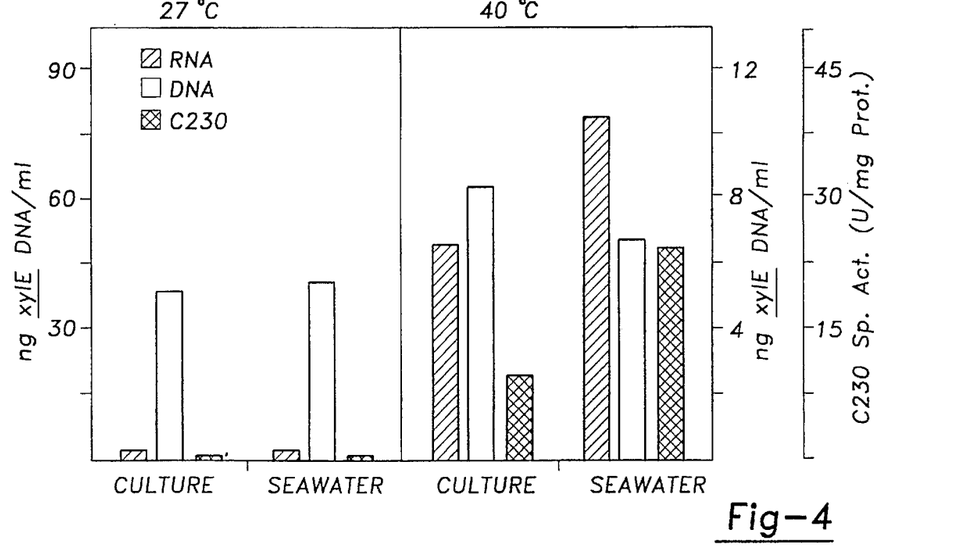
FIG. 4 shows detection of xylE expression in a marine Vibrio containing plasmid pLV1013 in culture and in cells resuspended in seawater. Cells at 27° C. show little or no xylE mRNA production or catechol dioxygenase (C2,30) activity while cells at 40° C. exhibited levels of both xylE mRNA and C2.30 activity. Changes in expression were not due to variation in xylE DNA (gene dose) as xylE DNA concentrations were nearly equal in both the 27° C. and 40° C. incubations.

The second gene used in the examples is the ribulose bisphosphate carboxylase (RuBPCase) large subunit gene (rbcL). This enzyme is involved in $CO_2$ fixation and plays an important role in controlling levels of one of the greenhouse gases, $CO_2$. FIG. 4 shows detection of xylE expression in Vibro cells that contained the temperature-regulated expression plasmid pLV1013. Cells were either taken directly from culture (abscissa labelled "culture") and assayed by the method described herein or else resuspended in seawater (abscissa labelled "seawater"). The hashed bar is level xylE mRNA, the open bar is level of xylE DNA, and the solid bar is the level of catechol dioxygenase enzyme activity.

Figure 5:
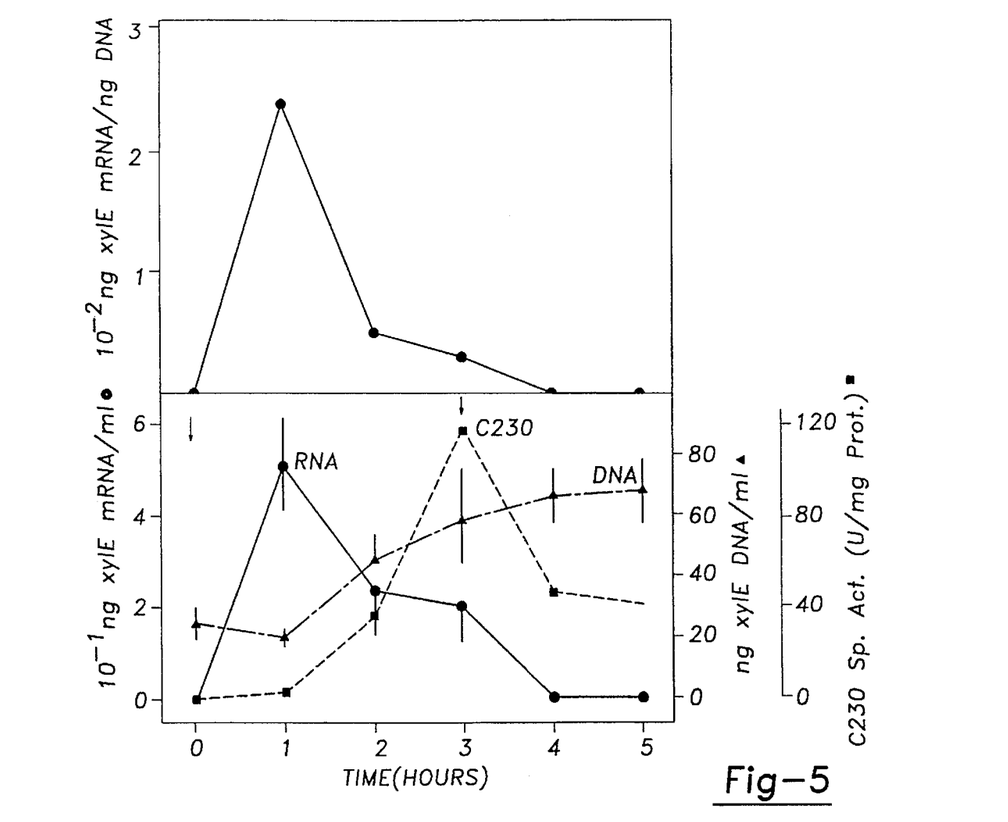
FIG. 5 shows induction of xylE gene expression in a marine Vibro sp. in response to temperature. Vibro sp containing a thermoregulated plasmid pLV1013 was grown at 27° C. Cells are shifted to 40° C. induction temperature at T=0 (first arrow), and then returned to 27° C. after 3 hours (second arrow). The top panel shows the kinetics of xylE mRNA accumulation over the induction period corrected for changes in gene dose (xylE mRNA/xylE DNA). The lower panel presents the changes in xylE mRNA (circles), xylE DNA (triangles) and catechol dioxygenase activity (squares)
Figure 6A:
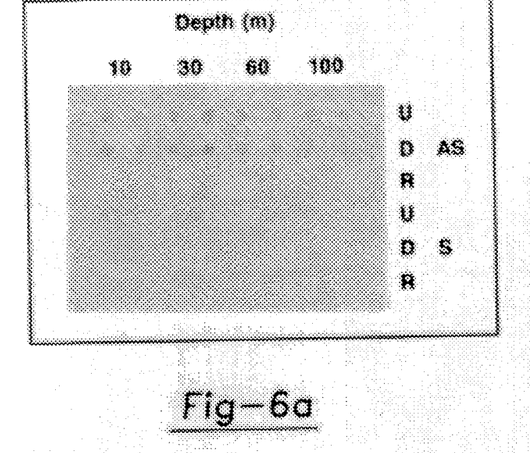
FIG. 6 shows overnight exposures of dot-blots of rbcL mRNA and DNA from 300 ml samples of station 6 seawater (FIG. 8) probed with a $^{35}$S-RNA rbcL probe. A) Vertical profile of rbcL mRNA. U=untreated, D-DNase, and R=RNases treatments. AS=antisense probe and S=sense probe. B) rbcL mRNA standard curve of decreasing amount of target sequence. C) Vertical profile of rbcL DNA. D) rbcL DNA standard curve with decreasing amounts of target sequence. Radioactivity is quantitated by an AMBIS Radioanalytic Imaging System.
Figure 6B:
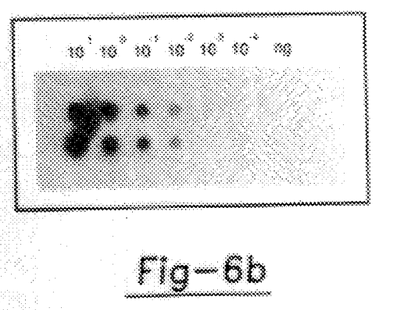
Figure 6C:
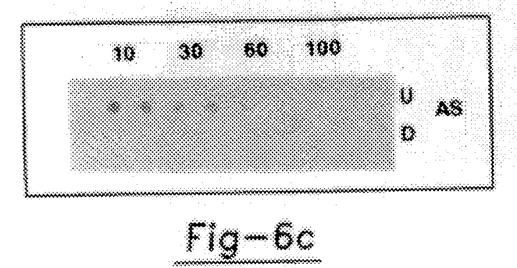
Figure 6D:
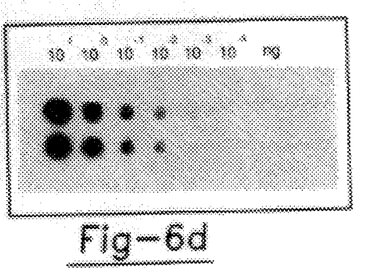
Figure 7A:
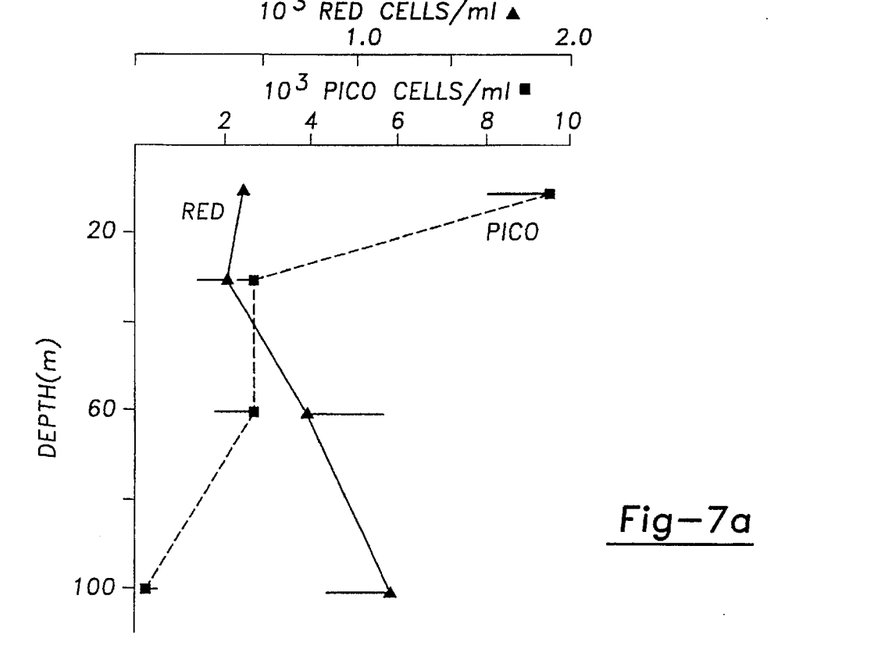
FIG. 7 shows vertical profiles of rbcL mRNA, DNA, carbon fixation, cells counts and chlorophyll for station 6. A) Relationship of picophytoplankton (squares) and red fluorescing cells (triangles). B) Vertical profile of photosynthetic carbon fixation (squares) under constant light to the vertical chlorophyll profile (circles). C) Vertical variation in rbcL mRNA (circles) and DNA (squares) levels. D) rbcL gene expression as mRNA/DNA (circles) correlates with carbon fixation/chlorophyll (triangles) at r=0.61.
Figure 7B:
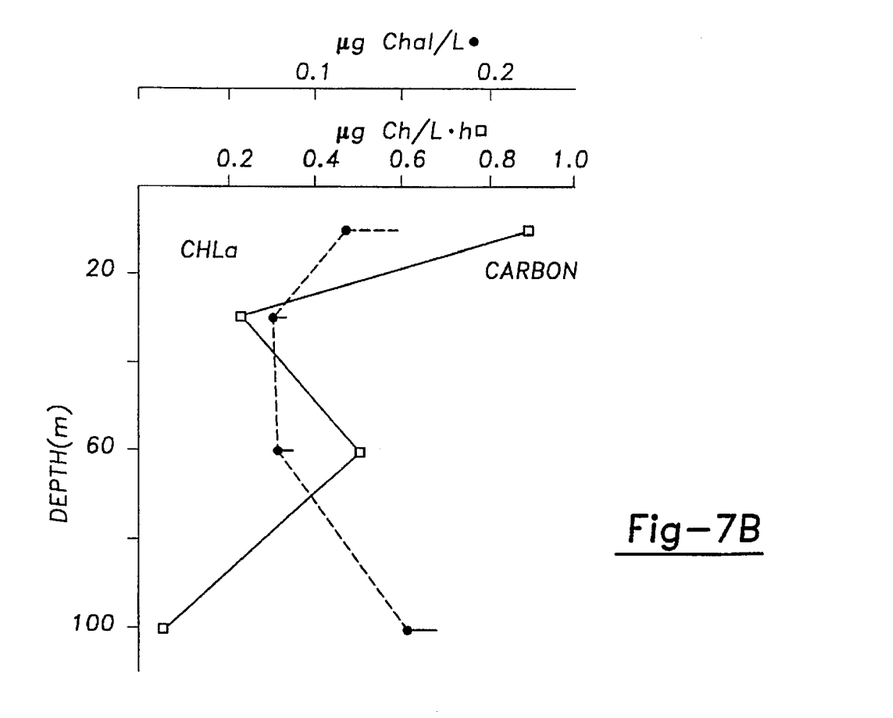
Figure 7C:
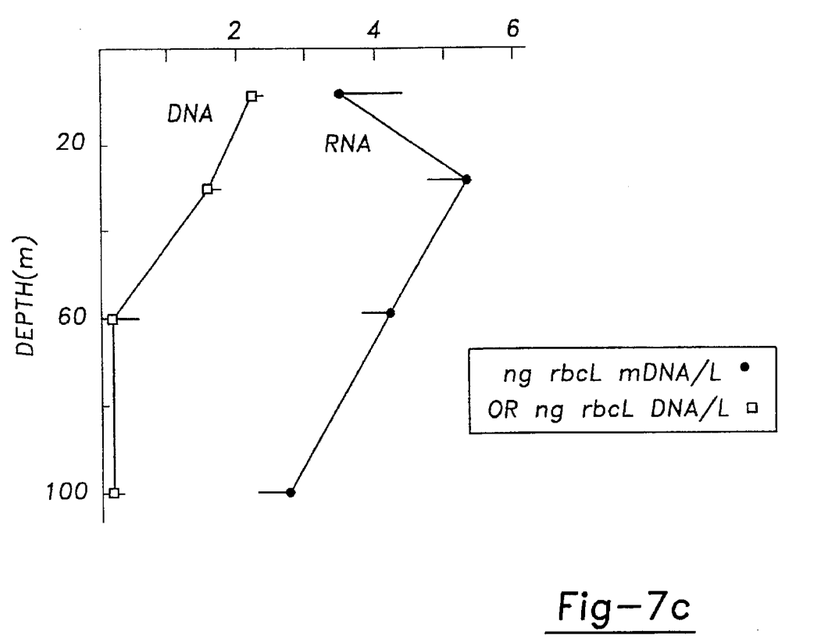
Figure 7D:
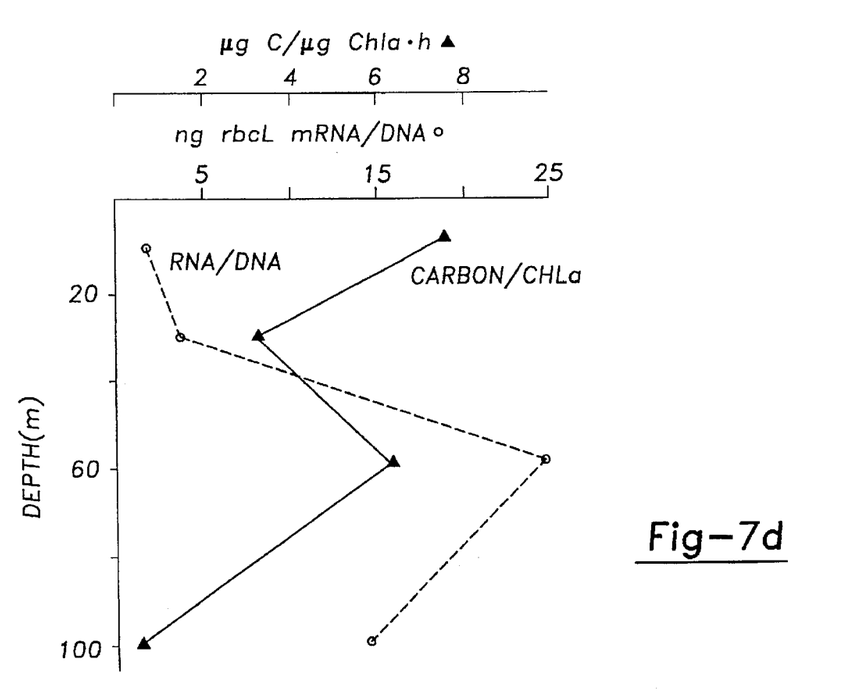

FIG. 5 clearly shows the utility of the mRNA per gene dose technology. xylE mRNA was immediately induced by a shift to 40° C., and then decreased when the cultures were shifted back to 28° C. The induction of mRNA was followed by production of catechol dioxygenase activity.

Figure 2:
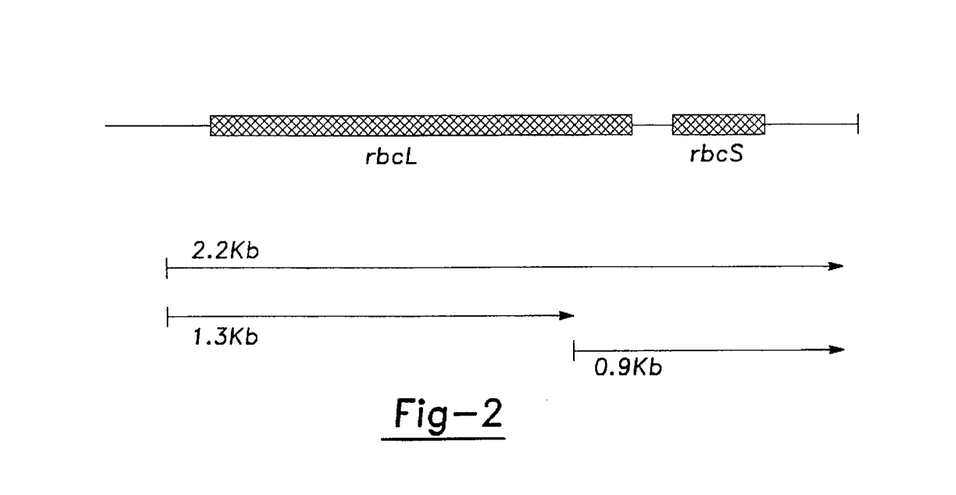
Figure 3A:
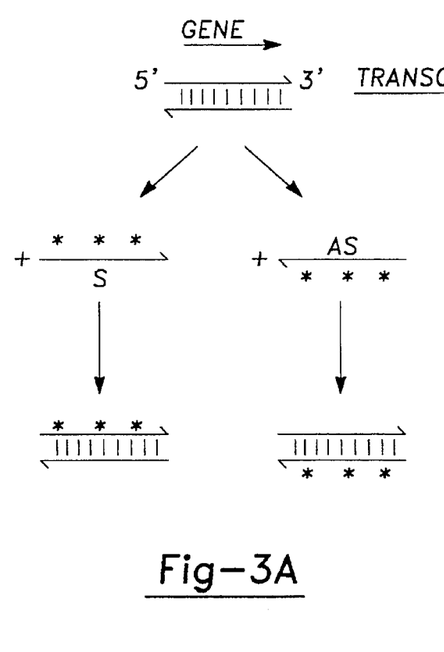
FIGS. 3A & B show hybridization characteristics of antisense and sense probes with A) DNA targets and B) mRNA targets. The antisense probe will hybridize with both RNA and DNA, whereas the sense probe will only bind with DNA. Thus the sense probe is used as a control for non-specific hybridization or contamination of RNA extracts with DNA.
Figure 3B:
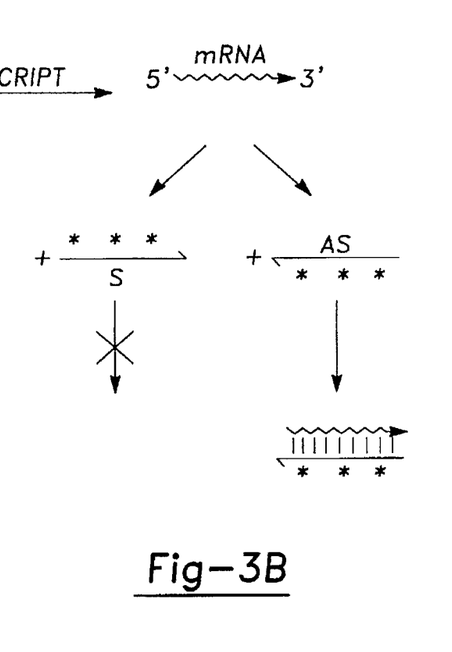

FIG. 6 shows a dot blot of mRNA and DNA extracts taken from samples of natural phytoplankton populations and probed with the rbcL probe. Samples were taken in duplicate at the depths indicated (i.e. "vertical profile"). Subsamples of the extracts were either untreated, DNase digested, or RNase digested (see Figure legend), and probed with the antisense (AS) or sense (S) single stranded RNA probes, that were generated as described in FIGS. 1, 2 and 3. Panel B is an rbcL mRNA standard curve, while Panel D is an rbcL DNA standard curve. Panel C shows dot blots of samples taken at the same depths and at the same time as those in Panel A, but extracted and probed for rbcL DNA.

FIG. 7 (Panels C and D) shows the data displayed in FIG. 6 after AMBIS detection of radioactivity. Also in FIG. 7 is corrolary information on the number of orange—fluorescing photosynthetic cells (Panel A), total photosynthetic pigment chlorophyll a (Panel B), carbon fixation as defined by $^{14}CO_2$ uptake (Panel B). Interestingly, in panel D the specific level of carbon fixation (carbon fixation per chlorophyll a) nearly mirrored the specific levels of gene expression (rbcL mRNA per rbcL DNA).

Figure 8A:
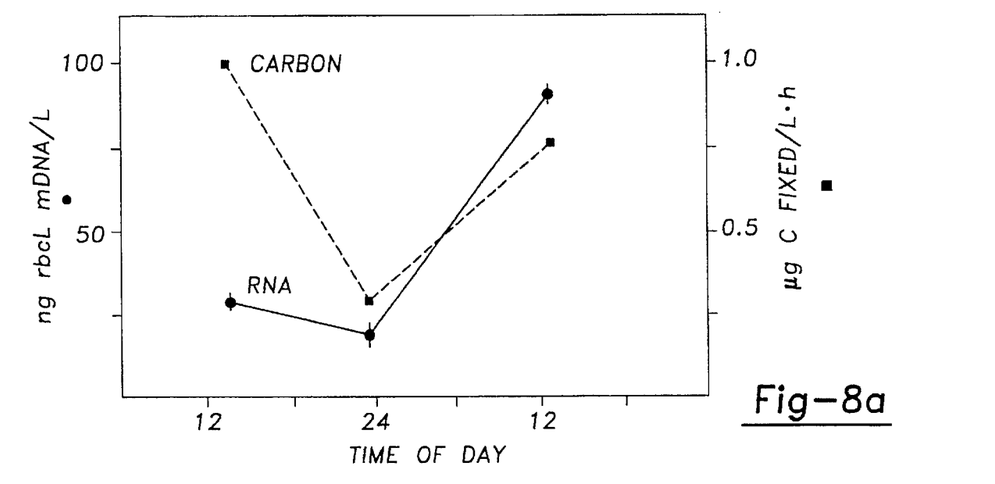
FIG. 8 shows Diel patterns in rbcL mRNA and DNA, carbon fixation and phytoplankton biomass in surface waters from station 3. 150 liters of water was incubated on deck under reduced natural light and at a rbcL gene expression as mRNA/DNA correlated with biomass normalized carbon fixation (r=0.96) suggesting that diel changes in carbon fixation appear to be regulated by changes in transcription of the rbcL gene in open ocean populations.
Figure 8B:
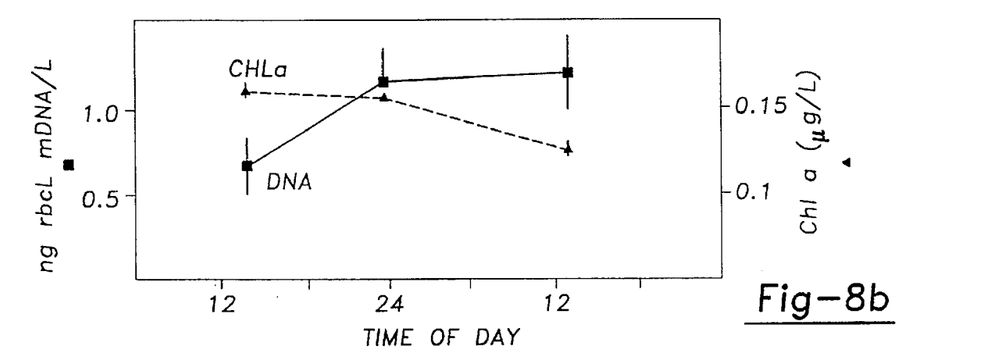
Figure 8C:
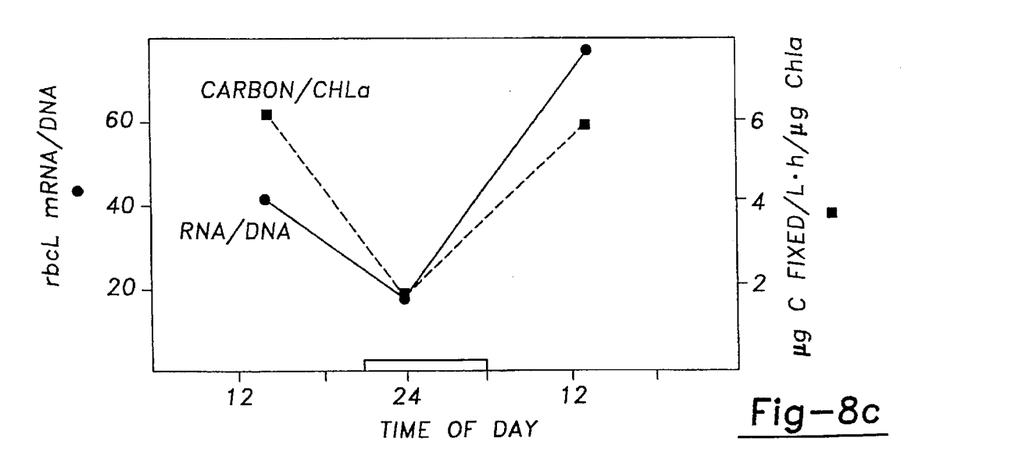

FIG. 8 shows the regulation of carbon fixation and rbcL gene expression for three samples over a 24 hour period. Photosynthetic carbon fixation is known to be highly regulated in response to light. This data shows that a change in photosynthetic carbon fixation also parallels changes in rbcL mRNA. This change in levels of carbon fixation and rbcL mRNA was not caused by changes in the photosynthetic population, because both rbcL DNA and chlorophyll a were relatively invariant over the three times sampled.

The above experiments demonstrate the utility of the present invention and the commercial potential for the present invention to be utilized in determining the effects of various stimuli in aquatic and nonaquatic environments.

The invention has been described in an illustrative manner, and it is to be understood that the terminology which has been used is intended to be in the nature of words of description rather than of limitation.

Obviously many modifications and variations of the present invention are possible in light of the above teachings. It is understood, therefore, the invention may be practiced otherwise than as specifically described.

What is claimed is:

1. A method of determining the level of transcription of a specific gene comprising the steps of:

(a) isolating mRNA from a population of microorganisms;

(b) isolating DNA from the population of microorganisms;

(c) quantifying the amount of a specific target mRNA in the isolated mRNA;

(d) quantifying the amount of a specific target DNA in the isolated DNA, the specific target DNA being the DNA from which the target mRNA is transcribed; and (e) dividing the amount of target mRNA by the amount of target DNA to determine the level of transcription of the target DNA as a measure of specific gene expression per gene dosage.

2. A method as set forth in claim 1, wherein the steps of quantifying the specific target mRNA and the specific target DNA include probing the isolated mRNA and the isolated DNA with a probe specific for the target mRNA and the target DNA.

3. A method as set forth in claim 2, wherein the isolated mRNA and the isolated DNA are separately divided into portions and the step of quantifying the specific target mRNA further includes probing one portion of the isolated mRNA with an antisense probe, probing a second portion of the isolated mRNA with a sense probe and subtracting a signal obtained using the sense probe from a signal obtained using the antisense probe, thereby controlling for nonspecific hybridization and contamination of the isolated mRNA with DNA.

4. A method as set forth in claim 3, wherein the sense and antisense probes are radiolabeled and each has the same total radioactivity.

5. A method as set forth in claim 1, wherein the population of microorganisms is a mixed population of microorganisms.

6. A method as set forth in claim 5, wherein the cells are procaryotic cells.

7. A method as set forth in claim 5, wherein the cells are eucaryotic cells.

8. A method of determining the level of transcription of a specific gene in response to a gene expression stimulus comprising the steps of:

(a) adding a gene expression stimulus to the environment of a population of microorganisms;

(b) isolating mRNA from the population of microorganisms;

(c) isolating DNA from the population of microorganisms;

(d) quantifying the amount of a specific target mRNA in the isolated mRNA;

(e) quantifying the amount of a specific target DNA in the isolated DNA, the specific target DNA being the DNA from which the target mRNA is transcribed;

(f) dividing the amount of target mRNA by the amount of target DNA to determine the level of transcription of the target DNA as a measure of specific gene expression per gene dosage in response to the gene expression stimulus; and (g) comparing the specific gene expression per gene dosage in response to the gene expression stimulus to the specific gene expression per gene dosage in the absence of the gene expression stimulus.

* * * * *